United States Patent
Akin et al.

(10) Patent No.: US 7,844,472 B1
(45) Date of Patent: Nov. 30, 2010

(54) METHOD AND SYSTEM FOR AGGREGATING AND STANDARDIZING HEALTHCARE QUALITY MEASURES

(75) Inventors: Muhammet Serdar Akin, Santa Clara, CA (US); Michael S. Klieman, Belmont, CA (US)

(73) Assignee: Intuit Inc., Mountain View, CA (US)

( * ) Notice: Subject to any disclaimer, the term of this patent is extended or adjusted under 35 U.S.C. 154(b) by 399 days.

(21) Appl. No.: 12/018,740

(22) Filed: Jan. 23, 2008

(51) Int. Cl.
G06Q 10/00 (2006.01)
G06Q 50/00 (2006.01)
(52) U.S. Cl. ................................. 705/2; 705/3; 705/11
(58) Field of Classification Search ................. 705/2–3, 705/7, 11
See application file for complete search history.

(56) References Cited

U.S. PATENT DOCUMENTS

| | | | |
|---|---|---|---|
| 2008/0133290 A1* | 6/2008 | Siegrist et al. ................. 705/7 |
| 2009/0043801 A1* | 2/2009 | LeClair et al. ............... 707/102 |
| 2009/0076855 A1* | 3/2009 | McCord ......................... 705/3 |
| 2009/0076868 A1* | 3/2009 | Malone et al. .................. 705/7 |
| 2009/0125348 A1* | 5/2009 | Rastogi ......................... 705/7 |

* cited by examiner

Primary Examiner—Luke Gilligan
(74) Attorney, Agent, or Firm—Gunnison, McKay & Hodgson, L.L.P.; Philip McKay

(57) ABSTRACT

A method and system for aggregating and standardizing healthcare quality ratings includes a process for aggregating and standardizing healthcare quality ratings whereby data representing healthcare provider quality ratings is obtained from one or more sources, i.e., parties offering and/or presenting healthcare provider quality ratings data. The data representing healthcare provider quality ratings obtained from one or more sources is then aggregated. The aggregated data representing healthcare provider quality ratings obtained from one or more sources is then standardized and/or normalized to provide a standardized and uniform ratings format/system. The normalized aggregated data representing healthcare provider quality ratings obtained from one or more sources is then stored, for access by authorized parties.

22 Claims, 2 Drawing Sheets

METHOD AND SYSTEM FOR AGGREGATING AND STANDARDIZING HEALTHCARE QUALITY MEASURES

BACKGROUND

Healthcare financing continues to be a significant problem in the United States. Healthcare costs are trending considerably above that of inflation. In 2002, healthcare spending in the United States increased 9.3 percent; the largest increase in 11 years. Healthcare spending in the United States increased an additional 7.8 percent in 2003, raising total healthcare spending to $1.7 trillion. According to a report issued by the Centers for Medicare and Medicaid Services, healthcare spending grew 5.7 percentage points faster than the overall United States economy in 2002, marking the fourth consecutive year in which the rate of healthcare spending surpassed growth in the rest of the United States economy.

As a result, employers and other providers of healthcare plans, as well as government officials and agencies, continue to seek ways to make patients more educated and careful consumers of healthcare. One recent innovation in this regard is consumer directed healthcare plans (CDHPs). However, it warrants repeating that virtually any measure designed to curb the skyrocketing healthcare costs will be highly reliant on patients, i.e., healthcare consumers, becoming more educated and value minded/results oriented consumers.

One important element needed to help healthcare consumers become more educated and value minded/results oriented is a mechanism whereby healthcare consumers can obtain information regarding the quality and/or historical performance of various healthcare providers, i.e., a healthcare provider ratings system and/or data source. However, the few currently available healthcare provider ratings systems and/or data sources are typically provided only through individual health plans, and/or third parties, who each use their own differing criteria for rating/evaluating healthcare providers and typically only provide information for healthcare providers in their respective plans or network. Consequently, there is no uniformity in these currently available healthcare provider ratings systems.

The lack of uniformity, or any type of cross over value, of healthcare provider ratings systems currently available has its roots in the fact that the healthcare "system" in the United States is, in reality, not a "system" at all. Rather, healthcare in the United States is a disconnected collection of large, medium and small medical businesses, healthcare providers and professionals, and large, medium and small healthcare provider and/or healthcare insurance provider organizations, along with third party groups that often have their own agendas.

As a result, to the average healthcare consumer, the currently available healthcare provider ratings systems are often viewed as being somewhat less than objective, at best, and often as deceptive, confusing and incredible time sinks that yield little in the way of useful results. Consequently, the currently available healthcare provider ratings systems do little to help, and arguably impede, efforts to create the more educated and value minded/results oriented healthcare consumers that are so critical to controlling healthcare spending in the United States.

SUMMARY

In accordance with one embodiment, a method and system for aggregating and standardizing healthcare quality ratings includes a process for aggregating and standardizing healthcare quality ratings whereby, in one embodiment, data representing healthcare provider quality ratings is obtained from one or more sources, i.e., parties offering and/or presenting healthcare provider quality ratings data. In one embodiment, the data representing healthcare provider quality ratings obtained from one or more sources is then aggregated and, in one embodiment, grouped according to the healthcare providers that are the subject of the data, and/or based on one or more other parameters. In one embodiment, the aggregated data representing healthcare provider quality ratings obtained from one or more sources is then standardized and/or normalized to create uniform ratings, in one embodiment, using one or more weighting factors created in accordance with one or more weighting parameters. In one embodiment, the normalized aggregated data representing healthcare provider quality ratings obtained from one or more sources is then stored, for access by authorized parties.

In one embodiment, all, or part of, the data representing healthcare provider quality ratings is obtained from one or more sources on a list of healthcare provider quality ratings sources created by, and/or for, the process for aggregating and standardizing healthcare quality ratings. In one embodiment, all, or part of, the data representing healthcare provider quality ratings is obtained from one or more user/healthcare consumer contribution systems, such as websites, that enable a user/healthcare consumer to review and/or rate healthcare providers. In one embodiment, the list of healthcare provider quality ratings sources includes, but is not limited to: healthcare insurance organizations; websites; public and private sources, such as government and watchdog organizations; community and special interest groups; academic organizations; third party ratings organizations; or any combination of these sources, or any other potential source of healthcare provider quality ratings data, whether known at the time of filing or as developed/made available thereafter.

In one embodiment, the list of healthcare provider quality ratings sources is obtained by entering the data into a user interface displayed on a computing system. In one embodiment, the list of healthcare provider quality ratings sources is obtained from, or through, a computing system implemented data management system, program, package or application that is a parent system for, or is associated with, the process for aggregating and standardizing healthcare quality ratings.

In one embodiment, all, or part of, the data representing healthcare provider quality ratings is obtained from one or more sources on the list of healthcare provider quality ratings either by transfer from the one or more sources on the list of healthcare provider quality ratings sources or by using screen scraping technology, or a similar technology, on any one or more of the following: a healthcare provider quality ratings source's healthcare/patient management system/application; a healthcare provider quality ratings source's healthcare/patient management web-site; a healthcare provider quality ratings source's healthcare provider management system/application; a healthcare provider quality ratings source's healthcare provider web-site; a general health information web-site; a health insurance system/application; a health insurance web-site; and/or any other system/application and/or web-site associated with one or more of the one or more healthcare provider quality ratings sources.

In some embodiments, all, or part of, the data representing healthcare provider quality ratings is obtained from any combination of the above sources and/or from any other source of data representing healthcare provider quality ratings, whether known at the time of filing or as developed thereafter.

In one embodiment, the data representing healthcare provider quality ratings obtained from one or more sources is then aggregated and, in one embodiment, grouped according to the healthcare providers that are the subject of the data, or based on one or more other parameters, such as performance related specific procedure and/or treatment provided. In one embodiment, the data representing healthcare provider quality ratings obtained from one or more sources is aggregated at a relatively high, i.e., less detailed level, such as, but not limited to, overall healthcare consumer satisfaction with the subject healthcare service provider. In one embodiment, the data representing healthcare provider quality ratings obtained from one or more sources is aggregated at a relatively detailed level, such, but not limited to, as specific performance, results, and/or experiences associated with the subject healthcare service provider. In one embodiment, the data representing healthcare provider quality ratings obtained from one or more sources is aggregated according to specific defined parameters.

In one embodiment, the aggregated data representing healthcare provider quality ratings obtained from one or more sources is then standardized and/or normalized to create single standardized and relatively uniform ratings framework/system. In one embodiment, the aggregated data representing healthcare provider quality ratings obtained from one or more sources is normalized by mapping various criteria and ratings systems/symbols of a given source ratings system to defined criteria and ratings systems/symbols. In one embodiment, the aggregated data representing healthcare provider quality ratings obtained from one or more sources is normalized, using one or more weighting factors created in accordance with one or more weighting parameters such as, but limited to, healthcare consumer feedback, regional correlations and/or considerations, the amount of ratings data available, or any other weighting parameter desired.

In one embodiment, the normalized aggregated data representing healthcare provider quality ratings obtained from one or more sources is then stored, in whole, or in part, in one or more databases maintained by, accessible by, owned by, or otherwise related to a provider of the process for aggregating and standardizing healthcare quality ratings, by any one of the numerous mechanisms known to those of skill in the art. In one embodiment, the normalized aggregated data representing healthcare provider quality ratings obtained from one or more sources, in whole, or in part, is stored/maintained by: the provider of the process for aggregating and standardizing healthcare quality ratings; a health insurance provider; a healthcare service provider; a third party data storage institution; any third party service or institution; or any other authorized parties.

In one embodiment, the normalized aggregated data representing healthcare provider quality ratings obtained from one or more sources is then accessed by authorized parties through an access portal, web-function, and/or application. In one embodiment, the process for aggregating and standardizing healthcare quality ratings is part of a computing system implemented data management system such as, but not limited to, a personal healthcare management, personal financial, business financial, accounting, or tax preparation data management system, program, package or application that implements, includes, is accessed by, and/or is otherwise associated with, the process for aggregating and standardizing healthcare quality ratings. In one embodiment, the normalized aggregated data representing healthcare provider quality ratings obtained from one or more sources is obtained by, or through, the computing system implemented data management system.

In one embodiment, parties given permission to access the data representing healthcare provider quality ratings obtained from one or more sources, i.e., authorized parties, are then provided access to all, or part, of the normalized aggregated data representing healthcare provider quality ratings obtained from one or more sources through a single account, access portal, and/or device.

Using the method and system for aggregating and standardizing healthcare quality ratings disclosed herein, healthcare consumers are provided standardized and uniform ratings of healthcare providers from one or more sources through a single, and in one embodiment, independent source. Consequently, the method and system for aggregating and standardizing healthcare quality ratings disclosed herein provides a tool to help create the more educated and value minded/results oriented healthcare consumers that are so critical to controlling healthcare spending in the United States.

As discussed in more detail below, using the below embodiments, with little or no modification and/or user input, there is considerable flexibility, adaptability, and opportunity for customization to meet the specific needs of various users under numerous circumstances.

Figure 1:
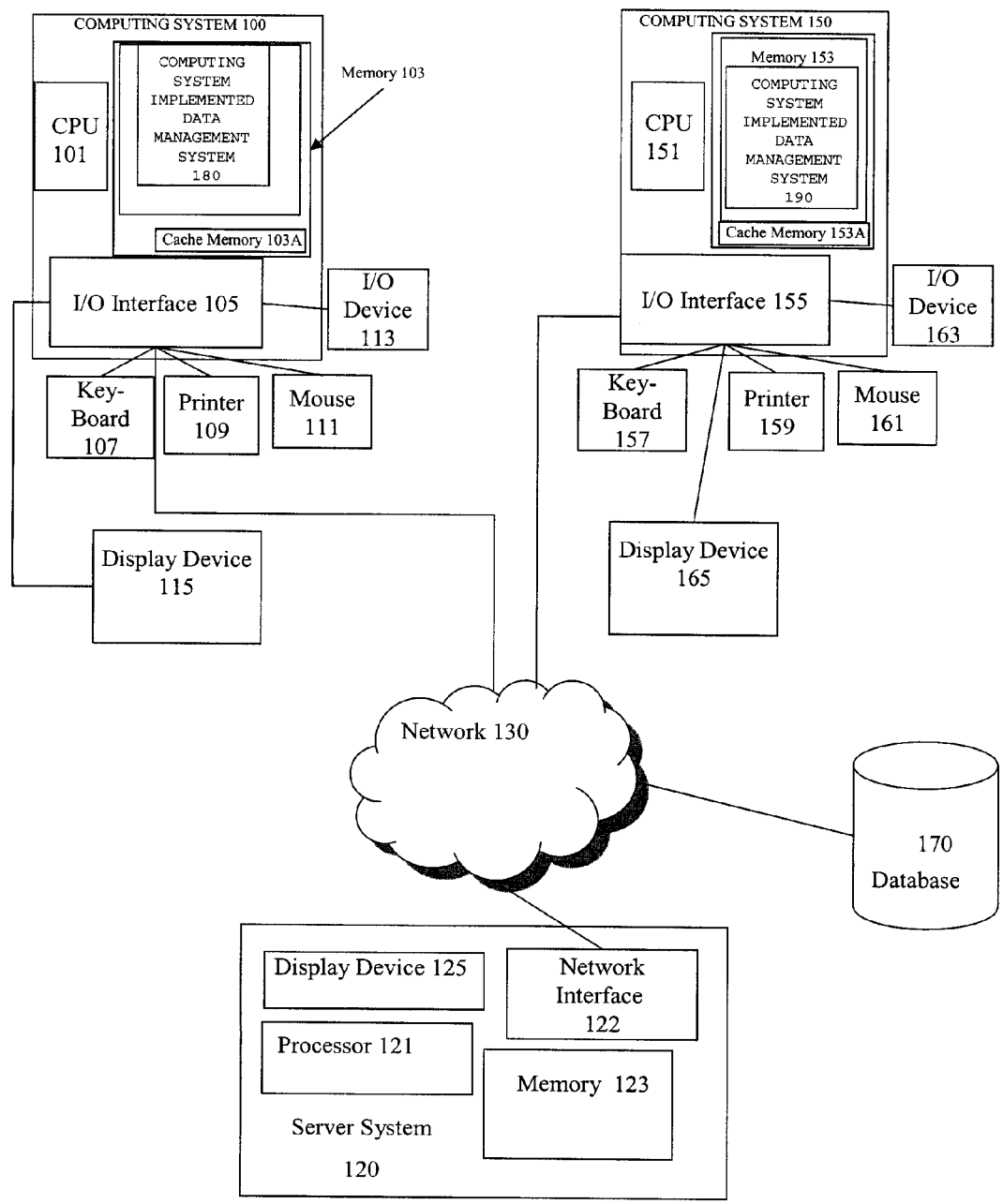
FIG. 1 is a block diagram of an exemplary hardware architecture for implementing one embodiment.

Common reference numerals are used throughout the FIGS. and the detailed description to indicate like elements. One skilled in the art will readily recognize that the above FIGS. are examples and that other architectures, modes of operation, orders of operation and elements/functions can be provided and implemented without departing from the characteristics and features of the invention, as set forth in the claims below.

DETAILED DESCRIPTION

Embodiments will now be discussed with reference to the accompanying FIGS., which depict one or more exemplary embodiments. Embodiments may be embodied in many different forms and should not be construed as limited to the embodiments set forth herein, shown in the FIGS., and/or described below. Rather, these exemplary embodiments are provided to allow a complete disclosure that conveys the principles of the invention, as set forth in the claims, to those of skill in the art.

Some embodiments are implemented in a computing system including a conventional computing system running a conventional operating system such as those distributed by Microsoft Corporation of Redmond Wash.; Apple Computer Inc. of Cupertino Calif.; any Unix operating system; any Linux operating system; the Palm OS series of operating systems; or any other operating system designed to generally manage operations on a computing system, whether known at the time of filing or as developed later. Some embodiments are implemented in a mobile computing system running mobile operating systems such as Symbian OS, Windows Mobile, or any other operating system designed to generally manage operations on a mobile computing system, whether known at the time of filing or as developed later. As described more fully below, embodiments can be implemented on computing systems other than a conventional computing system such as, for example, a personal digital assistant, a cell phone, or other computing system capable of processing computer readable data, whether known at the time of filing or as developed later. Computing systems also include those in which one or more computing resources (hardware or software) are located remotely and accessed via network, such as a Local Area Network (LAN), Wide Area Network (WAN), a public network, such as the Internet, a private network, a peer-to-peer network, a combination of network types, a computing system bus, or other electronic medium in which data may be exchanged between one computing system and one or more other computing system(s), whether known at the time of filing or as developed later. Embodiments may be included as add-on software for existing software system, programs, packages or applications, and embodiments may be a feature of an application that is bundled with a computing system or sold separately. Some embodiments may also be implemented as functionality embedded in hardware devices and systems.

Output generated by one or more embodiments can be displayed on a display screen, delivered from a website and/or web-based function, transmitted to a remote device, stored on any database, computer server or other storage mechanism, printed, or used in any other way. In addition, in some embodiments, processes and/or systems described herein may make use of input provided to the computer device implementing a process and/or application, discussed herein, via user interface devices such as a keyboard, mouse, touchpad, or any other device capable of providing user input to a computing system or for translating user actions into computing system operations, whether known at the time of filing or as developed later.

Hardware System Architecture

FIG. 1 is a block diagram of an exemplary hardware architecture for implementing one embodiment of a system and method for aggregating and standardizing healthcare quality ratings, such as exemplary process 200 discussed herein, that includes: a computing system 100, e.g., a first computing system; a computing system 150, e.g., a second computing system; a server system 120; and a database 170, all operatively coupled by a network 130.

As seen in FIG. 1, computing system 100 typically includes a central processing unit (CPU) 101, an input/output (I/O) interface 105, and a memory system 103, including cache memory 103A. In one embodiment, memory system 103 includes all, or part of, a computing system implemented data management system 180 such as, but not limited to: a computing system implemented healthcare management system; a computing system implemented personal financial management system; a computing system implemented business financial management system; a computing system implemented personal accounting system; a computing system implemented business accounting system; a computing system implemented tax preparation system; or any other computing system implemented personal and/or business data management system. In one embodiment, computing system implemented data management system 180 is stored, in whole, or in part, in memory system 103, and is used by, or includes, as discussed below, a process for aggregating and standardizing healthcare quality ratings, such as exemplary process 200 discussed below.

Computing system 100 may further include standard user interface devices such as a keyboard 107, a mouse 111, a printer 109, and a display device 115, as well as, one or more standard input/output (I/O) devices 113, such as a compact disk (CD) or Digital Video Disc (DVD) drive, floppy disk drive, or other digital or waveform port, or other device capable of inputting data to, and outputting data from, computing system 100, whether available or known at the time of filing or as later developed. As discussed in more detail below, in one embodiment, a process for aggregating and standardizing healthcare quality ratings and/or a computing system implemented data management system are entered, in whole, or in part, into computing system 100 via I/O device 113, such as from a CD, DVD, floppy disk, portable hard drive, memory stick, download site, or other medium and/or computer program product as defined herein.

In one embodiment, computing system 100 is a computing system used and/or accessible by another computing system, such as computing system 150 (discussed below), a workstation, a two-way pager, a cellular telephone, a smart phone, a digital wireless telephone, a Personal Digital Assistant (PDA), a server computer, an Internet appliance, any other device, or any desired combination of these devices, that includes components that can execute all, or part, of a process for aggregating and standardizing healthcare quality ratings, and/or a computing system implemented data management system, in accordance with at least one of the embodiments as described herein.

Similarly, computing system 150 typically includes a CPU 151, an input/output (I/O) interface 155, and a memory system 153, including cache memory 153A. Similar to computing system 100, computing system 150 may further include standard user interface devices such as a keyboard 157, a mouse 161, a printer 159, and a display device 165, as well as, one or more standard input/output (I/O) devices 163, such as a compact disk (CD) or DVD drive, floppy disk drive, or other digital or waveform port, or other device capable of inputting data to, and outputting data from, computing system 150, whether available or known at the time of filing or as later developed.

In one embodiment, memory system 153 includes all, or part of, a computing system implemented data management system 190 such as, but not limited to: a computing system implemented healthcare management system; a computing system implemented personal financial management system; a computing system implemented business financial management system; a computing system implemented personal accounting system; a computing system implemented business accounting system; a computing system implemented tax preparation system; or any other computing system implemented personal and/or business data management system.

As discussed in more detail below, in one embodiment, all, or part of, a process for aggregating and standardizing healthcare quality ratings, and/or a computing system implemented data management system, can be loaded, in whole, or in part, into computing system 150 from computing system 100 for storage in memory system 153 and/or cache memory 153A.

Also shown in FIG. 1 is exemplary database 170. In one embodiment, database 170 is a data storage device, a designated server system or computing system, or a designated portion of one or more server systems or computing systems, such as computing systems 100, 150 and 120, or a distributed database, or an external and/or portable hard drive. In one embodiment, database 170 is a dedicated mass storage device implemented in software, hardware, or a combination of hardware and software. In one embodiment, database 170 is a web-based function. As discussed in more detail below, in one embodiment, database 170 is under the control of the user, and/or the user's agents, and/or a process for aggregating and standardizing healthcare quality ratings, such as exemplary process 200, and/or a computing system implemented process, such as a computing system implemented data management system 180 and/or computing system implemented data management system 190.

In one embodiment, database 170 is used, controlled, and/or accessible by a provider of and/or a system and process for aggregating and standardizing healthcare quality ratings, such as process for aggregating and standardizing healthcare quality ratings 200 and data representing healthcare provider quality ratings obtained from one or more sources is stored in database 170. In one embodiment, database 170 is used, controlled, and/or accessible by a provider of and/or a computing system implemented data management system, such as a computing system implemented data management system 180 and/or computing system implemented data management system 190. In one embodiment, computing systems 100 and 150, and database 170, are coupled to a server system 120 through network 130. In one embodiment, server system 120 typically includes a server system display device 125, a server system processor 121, a server system memory 123, and a server system network interface 122.

In one embodiment, server system 120 is used in a station-to-station arrangement, such as a peer-to-peer, or hybrid peer-to peer, arrangement, as an indexing and/or central server used to connect a first computing system, such as computing system 100, and a second computing system, such as computing system 150.

Network 130 can be any network or network system that is of interest to a user such as, a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

Those of skill in the art will readily recognize that the components shown in FIG. 1, such as computing systems 100 and 150, database 170, server system 120, and their respective components, are shown for illustrative purposes only and that architectures with more or fewer components can implement, and benefit from, the invention. Moreover, one or more components of computing system 100, computing system 150, database 170, and server system 120 may be located remotely from their respective server system and accessed via network, as discussed herein. In addition, the particular type of, and configuration of, computing systems 100 and 150, database 170, and server system 120 are not relevant.

As discussed in more detail below, in one embodiment, a process for aggregating and standardizing healthcare quality ratings, such as process for aggregating and standardizing healthcare quality ratings 200, and/or a computing system implemented data management system, such as a computing system implemented data management system 180 and/or computing system implemented data management system 190, are stored, in whole, or in part, in memory system 103 and/or cache memory 103A, of computing system 100, and/or memory system 153 and/or cache memory 153A of computing system 150, and/or in server memory system 123 of server system 120 and/or in database 170, and executed on computing system 100 and/or computing system 150. As used herein, a memory refers to a volatile memory, a non-volatile memory, or any combination of the two.

Although a process for aggregating and standardizing healthcare quality ratings, such as process for aggregating and standardizing healthcare quality ratings 200, and/or a computing system implemented data management system, such as a computing system implemented data management system 180 and/or computing system implemented data management system 190, are sometimes referred to herein, alternatively, as a process, an application, a module, a program, a component of a software system, a component of a software package, a component of a parent system, a plug-in, or a feature of a parent system, this terminology is illustrative only. In some embodiments, a process for aggregating and standardizing healthcare quality ratings, such as process for aggregating and standardizing healthcare quality ratings 200, and/or a computing system implemented data management system, such as a computing system implemented data management system 180 and/or computing system implemented data management system 190, are capable of being called from an application or the operating system. In one embodiment, an application, process, or program is generally defined to be any executable code. Moreover, those of skill in the art will understand that when it is said that an application, process, or an operation takes some action, the action is the result of executing one or more instructions by a processor, such as CPUs 101 and 151, or server system processor 121. In one embodiment, execution of a process by CPU 101, CPU 151, or server system processor 121, results in the operations of an agent computer process (not shown) and/or a rule computer process (not shown).

In one embodiment, a process for aggregating and standardizing healthcare quality ratings, such as process for aggregating and standardizing healthcare quality ratings 200, and/or a computing system implemented data management system, such as a computing system implemented data management system 180 and/or computing system implemented data management system 190, and/or data representing healthcare provider quality ratings obtained from one or more sources, are computer applications or processes and/or data implemented and/or run and/or stored, in full, or in part, in, or on, a computer program product. Herein, a computer program product comprises a medium and/or I/O device configured to store or transport computer readable code, whether available or known at the time of filing or as later developed. Some examples of computer program products are CDs, DVDs, ROM cards, floppy discs, magnetic tapes, computer hard drives, portable hard drives, flash memory, volatile and non-volatile memory sticks, servers on a network, such as server system 120 of FIG. 1, and signals transmitted over a network, such as network 130 of FIG. 1, or other media or process capable of delivering computer readable data representing computer readable code, whether available or known at the time of filing or as later developed. This medium may belong to a computing system, such as computing systems 100 and 150 of FIG. 1, described above. However, in some embodiments, the medium also may be removable and/or remote from the computing system.

For example, all, or part, of a process for aggregating and standardizing healthcare quality ratings, such as process for aggregating and standardizing healthcare quality ratings 200, and/or a computing system implemented data management system, such as a computing system implemented data management system 180 and/or computing system implemented data management system 190, and/or data representing healthcare provider quality ratings obtained from one or more sources, may be stored in a memory that is physically located in a location, such as server system memory 123, or database 170, of FIG. 1, different from a computing system, such as computing systems 100 and/or 150 of FIG. 1, utilizing a process for aggregating and standardizing healthcare quality ratings, and/or a computing system implemented data management system. In one embodiment, all, or part, of a process for aggregating and standardizing healthcare quality ratings, and/or a computing system implemented data management system, may be stored in a memory that is physically located, separate from the computing system's processor(s), such as CPUs 101 and 151 of FIG. 1, and the computing system CPUs can be coupled to the memory in a client-server system, such as server system 120 of FIG. 1, or, alternatively, via connection to another computer, such as computing systems 100, 150 of FIG. 1, via modems and analog lines, digital interfaces and a digital carrier line, or wireless or cellular connections.

In one embodiment, the computing systems and/or server systems, such as computing systems 100 and/or 150 and/or server system 120 of FIG. 1, running and/or utilizing and/or storing all, or part, of a process for aggregating and standardizing healthcare quality ratings, such as process for aggregating and standardizing healthcare quality ratings 200, and/or a computing system implemented data management system, such as a computing system implemented data management system 180 and/or computing system implemented data management system 190, and/or data representing healthcare provider quality ratings obtained from one or more sources is a portable computer, a workstation, a two-way pager, a cellular telephone, a smart phone, a digital wireless telephone, a PDA, a server computer, an Internet appliance, or any other device that includes components that can execute all, or part, of a process for aggregating and standardizing healthcare quality ratings, and/or a computing system implemented data management system, in accordance with at least one of the embodiments as described herein. Similarly, in another embodiment, a process for aggregating and standardizing healthcare quality ratings, and/or a computing system implemented data management system, and/or data representing healthcare provider quality ratings obtained from one or more sources may be implemented on and/or run and/or stored on a computing system and/or server system that is comprised of multiple different computers, wireless devices, cellular telephones, digital telephones, two-way pagers, personal digital assistants, server computers, or any desired combination of these devices, that are coupled to perform the processes and/or operations as described herein.

Process

Herein, the terms "user", "healthcare consumer", "patient" and/or "customer" can be used interchangeably to denote a person who interfacing and/or otherwise interacting with a process for aggregating and standardizing healthcare quality ratings. Herein, the term "healthcare provider" and/or "healthcare service provider" denotes any individual person, persons, agencies, institutions, organizations, businesses, and/or other entities that provide medical treatment, medications, therapy, advice, and/or equipment. For example, herein, the term "healthcare provider" includes, but is not limited to: doctors; nurses; technicians; therapists; pharmacists; counselors; alternative medicine practitioners; medical facilities; doctor's offices; hospitals; emergency rooms; clinics; urgent care centers; alternative medicine clinics/facilities; physical therapy clinics/facilities; and any other entity providing general and/or specialized treatment, assessment, maintenance, therapy, medication, and/or advice relating to all, or any portion of, a healthcare consumer's state of health, including but not limited to: general medical, specialized medical, surgical, dental, vision, psychological, and/or any other type of treatment, assessment, maintenance, therapy, medication, and/or advice.

Herein, the term "healthcare" includes any general and/or specialized treatment, assessment, maintenance, therapy, medication, and/or advice relating to all, or any portion of, a healthcare consumer's state of health, including but not limited to: general medical, specialized medical, surgical, dental, vision, psychological, and/or any other type of treatment, assessment, maintenance, therapy, medication, and/or advice.

Herein, the term "medical treatment" includes, but is not limited to: one or more medications and/or medication regimes; physical therapy; recommended dietary changes; recommended activity level changes; other lifestyle changes; and/or surgical procedures; and/or any prescribed and/or suggested regime, medication, treatment, activity, avoided activity, and/or program designed to improve, maintain, and/or slow the degradation of, a healthcare consumer's health.

Herein, the term "healthcare benefit plan" and "health insurance plan" are used interchangeably to denote any policy, program, means and/or mechanism whereby a healthcare consumer is provided benefits and/or service and/or entitlements to any form of healthcare.

Herein, the terms "healthcare plan administrator", "healthcare benefit plan provider", "healthcare program administrator", and/or "employer" are used to denote any individual party, organization, or group that provides, presents, offers, pays for, in whole or in part, or is otherwise associated with giving a healthcare consumer access to one or more healthcare benefits, benefit plans, health insurance, and/or healthcare expense account programs.

In accordance with one embodiment, a method and system for aggregating and standardizing healthcare quality ratings includes a process for aggregating and standardizing healthcare quality ratings whereby, in one embodiment, data representing healthcare provider quality ratings is obtained from one or more sources, i.e., parties offering and/or presenting healthcare provider quality ratings data. In one embodiment, the data representing healthcare provider quality ratings obtained from one or more sources is then aggregated and, in one embodiment, grouped according to the healthcare providers that are the subject of the data, and/or based on one or more other parameters. In one embodiment, the aggregated data representing healthcare provider quality ratings obtained from one or more sources is then standardized and/or normalized, in one embodiment using one or more weighting factors created in accordance with one or more weighting parameters, to create single standardized and relatively uniform ratings framework/system. In one embodiment, the normalized aggregated data representing healthcare provider quality ratings obtained from one or more sources is then stored, for access by authorized parties through a access portal, web-function, and/or application.

Figure 2:
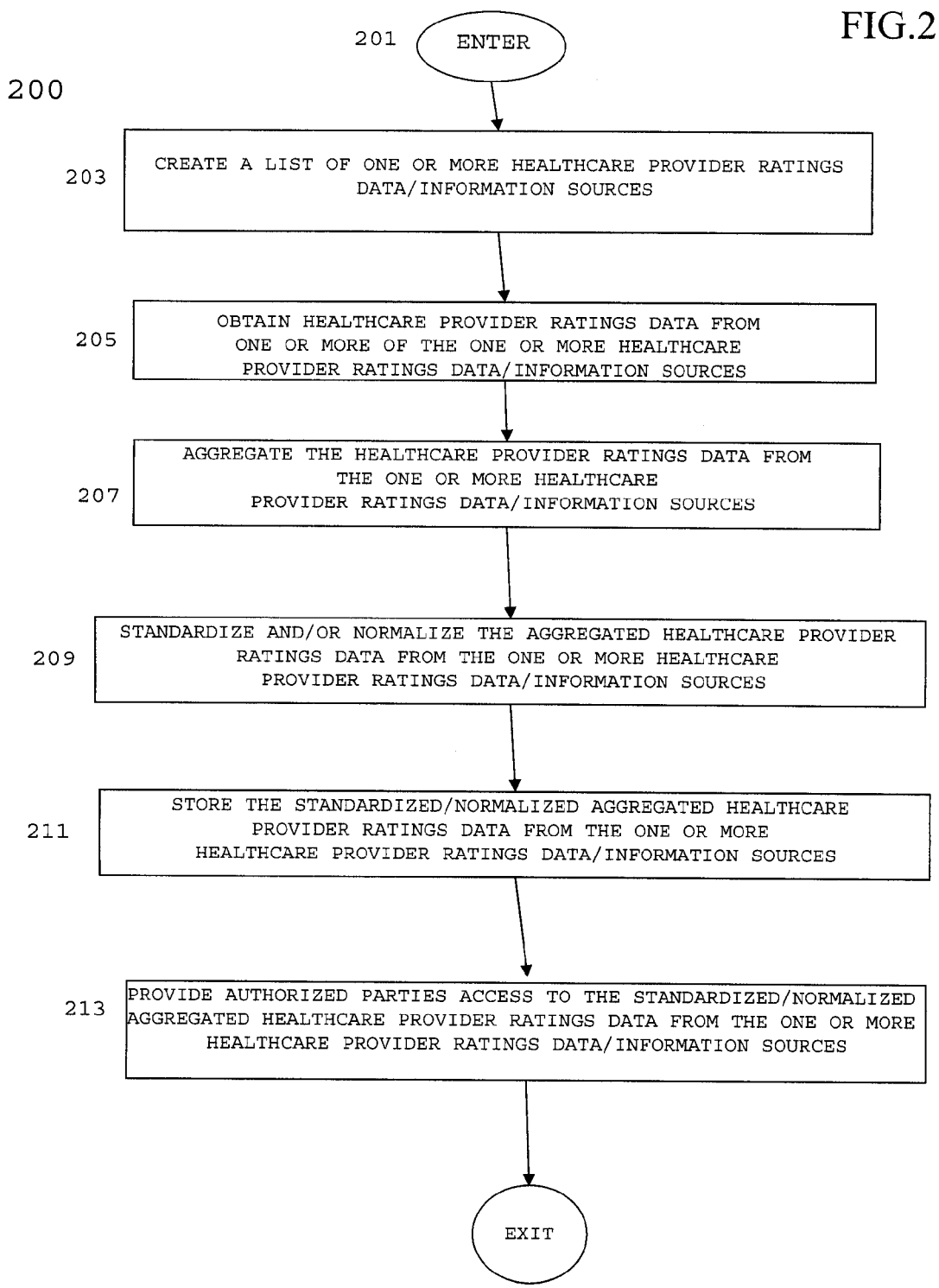
FIG. 2 is a flow chart depicting a process for aggregating and standardizing healthcare quality ratings in accordance with one embodiment.

FIG. 2 a flow chart depicting a process for aggregating and standardizing healthcare quality ratings 200 in accordance with one embodiment. Process for aggregating and standardizing healthcare quality ratings 200 begins at ENTER OPERATION 201 of FIG. 2 and process flow proceeds to CREATE A LIST OF ONE OR MORE HEALTHCARE PROVIDER RATINGS DATA/INFORMATION SOURCES OPERATION 203.

In one embodiment, at CREATE A LIST OF ONE OR MORE HEALTHCARE PROVIDER RATINGS DATA/INFORMATION SOURCES OPERATION 203 a list of one or more sources of healthcare provider ratings data is created/obtained.

In one embodiment, the list of one or more sources of healthcare provider ratings data of CREATE A LIST OF ONE OR MORE HEALTHCARE PROVIDER RATINGS DATA/INFORMATION SOURCES OPERATION 203 includes, but is not limited to: one or more health plan providers; one or more healthcare insurance organizations; one or more public and private sources, such as government and watchdog organizations; one or more community and special interest groups; one or more academic organizations; one or more third party healthcare provider ratings organizations; or any combination of these sources, or any other potential source of healthcare provider quality ratings, whether known at the time of filing or as developed/made available thereafter.

In one embodiment, the list of one or more sources of healthcare provider ratings data is obtained at CREATE A LIST OF ONE OR MORE HEALTHCARE PROVIDER RATINGS DATA/INFORMATION SOURCES OPERATION 203 by manual input and a user interface device, such as a keyboard, mouse, touch pad, voice recognition software, or any other means and/or mechanism for converting user actions into computing system processes.

In one embodiment, process for aggregating and standardizing healthcare quality ratings 200 is part of a personal healthcare management, personal financial, business financial, accounting, or tax preparation data management system, program, package or application, such as computing system implemented data management systems 180 and/or 190 of FIG. 1, that implements, includes, is accessed by, and/or is otherwise associated with process for aggregating and standardizing healthcare quality ratings 200. In one embodiment, the list of one or more sources of healthcare provider ratings data is obtained at CREATE A LIST OF ONE OR MORE HEALTHCARE PROVIDER RATINGS DATA/INFORMATION SOURCES OPERATION 203 from a computing system implemented data management system, such as computing system implemented data management system 180 and/or 190 of FIG. 1.

Returning to FIG. 2, in one embodiment, the list of one or more sources of healthcare provider ratings data is obtained at CREATE A LIST OF ONE OR MORE HEALTHCARE PROVIDER RATINGS DATA/INFORMATION SOURCES OPERATION 203 by any other method for obtaining a list of one or more sources of healthcare provider ratings data, whether known at the time of filing or as developed thereafter.

In one embodiment, once a list of one or more sources of healthcare provider ratings data is created/obtained at CREATE A LIST OF ONE OR MORE HEALTHCARE PROVIDER RATINGS DATA/INFORMATION SOURCES OPERATION 203, process flow proceeds to OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 data representing healthcare provider quality ratings is obtained from one or more of the one or more sources of healthcare provider ratings data on the list of CREATE A LIST OF ONE OR MORE HEALTHCARE PROVIDER RATINGS DATA/INFORMATION SOURCES OPERATION 203.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 the data representing healthcare provider quality ratings obtained from the one or more sources of healthcare provider ratings data on the list of CREATE A LIST OF ONE OR MORE HEALTHCARE PROVIDER RATINGS DATA/INFORMATION SOURCES OPERATION 203 includes, but is not limited to, data representing relatively general healthcare provider ratings such as overall healthcare consumer satisfaction with the subject healthcare service provider.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 the data representing healthcare provider quality ratings obtained from the one or more sources of healthcare provider ratings data on the list of CREATE A LIST OF ONE OR MORE HEALTHCARE PROVIDER RATINGS DATA/INFORMATION SOURCES OPERATION 203 includes, but is not limited to, data representing relatively detailed healthcare provider ratings data, such as specific performance, results, and/or experiences associated with the subject healthcare service provider.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 the data representing healthcare provider quality ratings obtained from the one or more sources of healthcare provider ratings data on the list of CREATE A LIST OF ONE OR MORE HEALTHCARE PROVIDER RATINGS DATA/INFORMATION SOURCES OPERATION 203 includes any level of detail and/or healthcare service provider rating criteria desired and/or available from any of the one or more sources of healthcare provider ratings data on the list of CREATE A LIST OF ONE OR MORE HEALTHCARE PROVIDER RATINGS DATA/INFORMATION SOURCES OPERATION 203.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION by transfer from the one or more sources on the list of healthcare provider quality ratings.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION 203 using screen scraping technology on web-sites and/or display screens controlled and/or generated the one or more sources of healthcare provider ratings data on the list of CREATE A LIST OF ONE OR MORE HEALTHCARE PROVIDER RATINGS DATA/INFORMATION SOURCES OPERATION 203.

Screen scraping technology is well known to those of skill in the art. Screen scraping is a technique in which a computing system implemented process, such as process for aggregating and standardizing healthcare quality ratings 200, interacts with/links with a specific application that extracts data, such as healthcare service provider rating data, from the display of another program or site, such as a program and/or site controlled and/or provided by any of the one or more sources of healthcare provider ratings data on the list of CREATE A LIST OF ONE OR MORE HEALTHCARE PROVIDER RATINGS DATA/INFORMATION SOURCES OPERATION 203.

One element that distinguishes screen scraping from other forms of parsing data is that the output data being scraped was originally intended for final display to a human user, rather than as input to another program such as process for aggregating and standardizing healthcare quality ratings 200. Therefore, the output data being scraped is usually neither documented nor structured for convenient parsing.

There are a number of synonyms for screen scraping, including: data scraping, data extraction, web scraping, page scraping, web page wrapping and HTML scraping (the last four being specific to scraping web pages). Currently, screen scraping is most often done to either: (1) interface to a legacy system which has no other mechanism compatible with current hardware; or (2) interface to a third-party system which does not provide a more convenient API. In one embodiment, the one or more sources of healthcare provider ratings data on the list of CREATE A LIST OF ONE OR MORE HEALTHCARE PROVIDER RATINGS DATA/INFORMATION SOURCES OPERATION 203 represent the second case above in that one or more of the web-sites and/or screen displays provided by the one or more sources of healthcare provider ratings data on the list of CREATE A LIST OF ONE OR MORE HEALTHCARE PROVIDER RATINGS DATA/INFORMATION SOURCES OPERATION 203 may have no other, or no common, data parsing mechanism/API available.

As noted above, means, mechanisms, processes and procedures for implementing and using screen scraping technology are well known to those of skill in the art. Consequently, a more detailed discussion of means, mechanisms, processes and procedures for implementing and using screen scraping technology is omitted here to avoid detracting from the invention.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION 203 using screen scraping technology, or a similar technology on any one or more of the following: a healthcare provider quality ratings source's healthcare/patient management system/application; a healthcare provider quality ratings source's healthcare/patient management web-site; a healthcare provider quality ratings source's healthcare provider management system/application; a healthcare provider quality ratings source's healthcare provider web-site; a general health information web-site; a health insurance system/application; a health insurance web-site; and/or any other system/application and/or web-site associated with one or more of the one or more healthcare provider quality ratings sources of CREATE A LIST OF ONE OR MORE HEALTHCARE PROVIDER RATINGS DATA/INFORMATION SOURCES OPERATION 203.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION 203 by a combination of transfer from the one or more sources on the list of healthcare provider quality ratings and screen scraping and/or by any other method and/or means for obtaining the data representing healthcare provider quality ratings from the one or more sources of healthcare provider ratings data on the list of CREATE A LIST OF ONE OR MORE HEALTHCARE PROVIDER RATINGS DATA/INFORMATION SOURCES OPERATION 203 whether known at the time of filing or as developed thereafter.

For instance, in one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION 203 by entering the data into a user interface displayed on a computing system, such as computing system 100 described above.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION 203 through an access port and/or account using an assigned personal identification number or code.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION 203 by providing access to the data on a computer program product as defined herein.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION 203 through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a station-to-station network, peer-to-peer network, Local Area Network (LAN), a Wide Area Network (WAN), a public network, such as the Internet, a private network, a combination of network types, or other network capable of allowing communication between two or more computing systems, whether available or known at the time of filing or as later developed.

In one embodiment, at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 all, or part, of the data representing healthcare provider quality ratings is obtained from the one or more sources of healthcare provider ratings data on the list of CREATE A LIST OF ONE OR MORE HEALTHCARE PROVIDER RATINGS DATA/ INFORMATION SOURCES OPERATION 203 through any method, apparatus, process or mechanism for transferring data and/or text from one or more devices, computing systems, server systems, databases, web site/web functions and/ or any devices having a data storage/processing capability to one or more other devices, computing systems, server systems, databases, web site/web functions and/or any devices having a data storage/processing capability, whether known at the time of filing or as thereafter developed.

In one embodiment, once data representing healthcare provider quality ratings is obtained from the one or more sources of healthcare provider ratings data on the list of CREATE A LIST OF ONE OR MORE HEALTHCARE PROVIDER RATINGS DATA/INFORMATION SOURCES OPERATION 203 at OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205, process flow proceeds to AGGREGATE THE HEALTHCARE PROVIDER RATINGS DATA FROM THE ONE OR MORE HEALTHCARE PROVIDER RATINGS DATA/INFORMATION SOURCES OPERATION 207.

In one embodiment, at AGGREGATE THE HEALTHCARE PROVIDER RATINGS DATA FROM THE ONE OR MORE HEALTHCARE PROVIDER RATINGS DATA/INFORMATION SOURCES OPERATION 207 the data representing healthcare provider quality ratings obtained from one or more sources of OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 is aggregated and, in one embodiment, grouped according to the healthcare providers that are the subject of the data, and/or based on one or more other aggregation parameters.

In one embodiment, at AGGREGATE THE HEALTHCARE PROVIDER RATINGS DATA FROM THE ONE OR MORE HEALTHCARE PROVIDER RATINGS DATA/INFORMATION SOURCES OPERATION 207 the data representing healthcare provider quality ratings obtained from one or more sources of OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 is aggregated at a relatively high, i.e., less detailed level, such as, but not limited to, overall healthcare consumer satisfaction with the subject healthcare service provider. In one embodiment, the data representing healthcare provider quality ratings obtained from one or more sources is aggregated at a relatively detailed level, such, such as, but not limited to, specific performance, results, and/or experiences associated with the subject healthcare service provider. In one embodiment, the data representing healthcare provider quality ratings obtained from one or more sources is aggregated according to specific defined parameters/criteria desired by the provider of process for aggregating and standardizing healthcare quality ratings 200 and/or the healthcare service consumer.

In one embodiment, at AGGREGATE THE HEALTHCARE PROVIDER RATINGS DATA FROM THE ONE OR MORE HEALTHCARE PROVIDER RATINGS DATA/INFORMATION SOURCES OPERATION 207 the data representing healthcare provider quality ratings obtained from one or more sources of OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 is aggregated and/or correlated to a given healthcare service provider by electronically attaching a unique code associated with the healthcare service provider.

In one embodiment, at AGGREGATE THE HEALTHCARE PROVIDER RATINGS DATA FROM THE ONE OR MORE HEALTHCARE PROVIDER RATINGS DATA/INFORMATION SOURCES OPERATION 207 the data representing healthcare provider quality ratings obtained from one or more sources of OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 is aggregated and/or correlated to a given healthcare service provider by saving the data in one or more locations/accounts uniquely associated with the healthcare service provider in question.

In one embodiment, once the data representing healthcare provider quality ratings obtained from one or more sources of OBTAIN HEALTHCARE PROVIDER RATINGS DATA FROM ONE OR MORE OF THE ONE OR MORE HEALTHCARE PROVIDER RATINGS DATA/INFORMATION SOURCES OPERATION 205 is aggregated at AGGREGATE THE HEALTHCARE PROVIDER RATINGS DATA FROM THE ONE OR MORE HEALTHCARE PROVIDER RATINGS DATA/INFORMATION SOURCES OPERATION 207, process flow proceeds to STANDARDIZE AND/OR NORMALIZE THE AGGREGATED HEALTHCARE PROVIDER RATINGS DATA FROM THE ONE OR MORE HEALTHCARE PROVIDER RATINGS DATA/INFORMATION SOURCES OPERATION 209.

In one embodiment, at STANDARDIZE AND/OR NORMALIZE THE AGGREGATED HEALTHCARE PROVIDER RATINGS DATA FROM THE ONE OR MORE HEALTHCARE PROVIDER RATINGS DATA/INFORMATION SOURCES OPERATION 209 the aggregated data representing healthcare provider quality ratings obtained from one or more sources is then standardized and/or normalized to create a single and relatively uniform ratings format and/or system.

In one embodiment, at STANDARDIZE AND/OR NORMALIZE THE AGGREGATED HEALTHCARE PROVIDER RATINGS DATA FROM THE ONE OR MORE HEALTHCARE PROVIDER RATINGS DATA/INFORMATION SOURCES OPERATION 209 the aggregated data representing healthcare provider quality ratings obtained from one or more sources is standardized by mapping various criteria and ratings systems/symbols of a given source ratings system to defined criteria and ratings systems/symbols used with process for aggregating and standardizing healthcare quality ratings 200.

In one embodiment, at STANDARDIZE AND/OR NORMALIZE THE AGGREGATED HEALTHCARE PROVIDER RATINGS DATA FROM THE ONE OR MORE HEALTHCARE PROVIDER RATINGS DATA/INFORMATION SOURCES OPERATION 209 the aggregated data representing healthcare provider ratings obtained from one or more sources is normalized using one or more weighting factors created in accordance with one or more weighting parameters.

In one embodiment, the one or more weighting parameters include, but are not limited to: healthcare consumer feedback and comparison of the healthcare consumer feedback to the healthcare service provider ratings data from the respective source of the healthcare service provider ratings data of CREATE A LIST OF ONE OR MORE HEALTHCARE PROVIDER RATINGS DATA/INFORMATION SOURCES OPERATION 203; regional correlations and/or considerations associated with the healthcare service provider ratings data; the amount of healthcare service provider ratings data available about a given healthcare service provider; or any other weighting parameter desired.

Means, mechanisms, processes and procedures for implementing and using weighting factors and processing data including weighting factors are well known to those of skill in the art. Consequently, a more detailed discussion of means, mechanisms, processes and procedures for implementing and using weighting factors is omitted here to avoid detracting from the invention.

In one embodiment, once the aggregated data representing healthcare provider quality ratings obtained from one or more sources is standardized and/or normalized to create uniform ratings at STANDARDIZE AND/OR NORMALIZE THE AGGREGATED HEALTHCARE PROVIDER RATINGS DATA FROM THE ONE OR MORE HEALTHCARE PROVIDER RATINGS DATA/INFORMATION SOURCES OPERATION 209, process flow proceeds to STORE THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 211.

In one embodiment, at STORE THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 211, the standardized and/or normalized aggregated data representing healthcare provider quality ratings obtained from one or more sources is stored, in whole, or in part, in a database and/or memory maintained by, accessible by, owned by, or otherwise related to, a provider of process for aggregating and standardizing healthcare quality ratings 200 by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet.

Returning to FIG. 2, in some embodiments, the data stored as described above is maintained, in whole, or in part, by: the healthcare consumer; the provider of process for aggregating and standardizing healthcare quality ratings 200; a health insurance provider; a provider of a computing system implemented data management system, such as computing system implemented data management systems 180 and/or 190 of FIG. 1; a healthcare service provider; any of the healthcare data/information providers; a third party data storage institution; any third party service or institution; or any other parties.

In one embodiment, once the standardized and/or normalized aggregated data representing healthcare provider quality ratings obtained from one or more sources is stored at STORE THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 211, process flow proceeds to PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213.

In one embodiment, at PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213 the standardized and/or normalized aggregated data representing healthcare provider quality ratings obtained from one or more sources is made available to authorized parties, i.e., authorized healthcare service consumers.

In one embodiment, at PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213 the standardized and/or normalized aggregated data representing healthcare provider quality ratings obtained from one or more sources is made available to authorized healthcare service consumers through an access portal, web-function, and/or application.

As noted above, in one embodiment, process for aggregating and standardizing healthcare quality ratings 200 is part of a computing system implemented data management system such as, but not limited to, a personal healthcare management, personal financial, business financial, accounting, or tax preparation data management system, program, package or application that implements, includes, is accessed by, and/or is otherwise associated with, process for aggregating and standardizing healthcare quality ratings 200. In one embodiment, at PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213 the standardized and/or normalized aggregated data representing healthcare provider quality ratings obtained from one or more sources is made available to authorized healthcare service consumers through one or more computing system implemented data management system.

In one embodiment, at PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213 the standardized and/or normalized aggregated data representing healthcare provider quality ratings obtained from one or more sources is made available to authorized healthcare service consumers by providing access to the data through the a healthcare consumer's account using an assigned personal identification number or code.

In one embodiment, at PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213 the standardized and/or normalized aggregated data representing healthcare provider quality ratings obtained from one or more sources is made available to authorized healthcare service consumers by providing access to the data on a computer program product as defined herein.

In one embodiment, at PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213 the standardized and/or normalized aggregated data representing healthcare provider quality ratings obtained from one or more sources is made available to authorized healthcare service consumers through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a station-to-station network, peer-to-peer network, Local Area Network (LAN), a Wide Area Network (WAN), a public network, such as the Internet, a private network, a combination of network types, or other network capable of allowing communication between two or more computing systems, whether available or known at the time of filing or as later developed.

In one embodiment, at PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213 the standardized and/or normalized aggregated data representing healthcare provider quality ratings obtained from one or more sources is made available to authorized healthcare service consumers through any method, apparatus, process or mechanism for transferring data and/or text from one or more devices, computing systems, server systems, databases, web site/web functions and/or any devices having a data storage/processing capability to one or more other devices, computing systems, server systems, databases, web site/web functions and/or any devices having a data storage/processing capability, whether known at the time of filing or as thereafter developed.

In one embodiment, once the standardized and/or normalized aggregated data representing healthcare provider quality ratings obtained from one or more sources is made available to authorized healthcare service consumers at PROVIDE AUTHORIZED PARTIES ACCESS TO THE STANDARDIZED/NORMALIZED AGGREGATED HEALTHCARE PROVIDER RATINGS DATA FROM THE ONE OR MORE HEALTHCARE PROVIDER RATINGS DATA/INFORMATION SOURCES OPERATION 213 process flow proceeds to EXIT OPERATION 230 and process for aggregating and standardizing healthcare quality ratings 200 is exited to await new data and or a new iteration of process for aggregating and standardizing healthcare quality ratings 200.

Using process for aggregating and standardizing healthcare quality ratings 200, healthcare consumers are provided standardized and uniform ratings of healthcare providers from one or more sources through a single, and in one embodiment, independent source. Consequently, process for aggregating and standardizing healthcare quality ratings 200 provides a tool to help create the more educated and value minded/results oriented healthcare consumers that are so critical to controlling healthcare spending in the United States.

As discussed in more detail above, using the above embodiments, with little or no modification and/or user input, there is considerable flexibility, adaptability, and opportunity for customization to meet the specific needs of various users under numerous circumstances.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "defining", "creating", "aggregating", "standardizing", "normalizing", "accessing", "obtaining", "transferring", "storing", "providing", etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIGS. are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented process for aggregating and standardizing healthcare quality ratings comprising:
   A processor; and
   A memory coupled to the processor, the memory having stored therein processor executable instructions which when executed by the processor perform a process for aggregating and standardizing healthcare quality ratings comprising:
   obtaining healthcare service provider ratings data from two or more different sources of healthcare service provider ratings data, the two or more different sources of healthcare service provider ratings data having different rating systems and being selected from at least one of the group of sources of healthcare service provider ratings data consisting of:
   a healthcare plan provider,
   a healthcare insurance provider,
   a healthcare service provider,
   a third party rating system, and
   a healthcare consumer based healthcare service provider rating system;
   aggregating the healthcare service provider ratings data from the two or more sources of healthcare service provider ratings data;
   standardizing the aggregated healthcare service provider ratings data from the two or more sources of healthcare service provider ratings data by mapping ratings criteria from the two or more ratings systems of the two or more sources of healthcare service provider ratings data to a single ratings system;
   providing healthcare consumers access to the standardized aggregated healthcare service provider ratings data from the two or more sources of healthcare service provider ratings data.

2. The computing system for aggregating and standardizing healthcare quality ratings of claim 1, wherein;
   at least part of the healthcare service provider ratings data is obtained from at least one of the two or more sources of healthcare service provider ratings data by data transfer from the at least one of the two or more sources of healthcare service provider ratings data.

3. The computing system for aggregating and standardizing healthcare quality ratings of claim 1, wherein;
   at least part of the healthcare service provider ratings data obtained from the two or more sources of healthcare service provider ratings data is obtained using screen scraping technology.

4. The computing system for aggregating and standardizing healthcare quality ratings of claim 3, wherein;
   at least part of the healthcare service provider ratings data obtained from the two or more sources of healthcare service provider ratings data is obtained from application output data of at least one application associated with at least one source of healthcare service provider ratings data using screen scraping technology.

5. The computing system for aggregating and standardizing healthcare quality ratings of claim 3, wherein;
   at least part of the healthcare service provider ratings data obtained from the two or more sources of healthcare service provider ratings data is obtained from least one web-site associated with at least one source of healthcare service provider ratings data using screen scraping technology.

6. The computing system for aggregating and standardizing healthcare quality ratings of claim 1, wherein;
   aggregating the healthcare service provider ratings data from the two or more sources of healthcare service provider ratings data comprises aggregating the healthcare service provider ratings data in accordance with one or more aggregation parameters.

7. The computing system for aggregating and standardizing healthcare quality ratings of claim 1, wherein;
   standardizing the aggregated healthcare service provider ratings data from the two or more sources of healthcare service provider ratings data comprises normalizing the aggregated healthcare service provider ratings data from the two or more sources of healthcare service provider ratings data.

8. The computing system for aggregating and standardizing healthcare quality ratings of claim 7, wherein;
   the aggregated healthcare service provider ratings data from the two or more sources of healthcare service provider ratings data is normalized using one or more weighting factors based on one or more weighting parameters.

9. The computing system for aggregating and standardizing healthcare quality ratings of claim 8, wherein;
   the one or more weighting parameters include one or more of the following weighting parameters:
   healthcare consumer feedback and comparison of the healthcare consumer feedback to the healthcare service provider ratings data from the respective source of the healthcare service provider ratings data;
   regional comparisons and/or considerations associated with the healthcare service provider ratings data; or
   the amount of healthcare service provider ratings data available about a given healthcare service provider.

10. The computing system for aggregating and standardizing healthcare quality ratings of claim 1, wherein;
    providing healthcare consumers access to the standardized aggregated healthcare service provider ratings data from the two or more sources of healthcare service provider ratings data comprises storing the standardized aggregated healthcare service provider ratings data from the two or more sources of healthcare service provider ratings data in one or more databases and providing the authorized healthcare consumers access to the one or more databases.

11. A computer program product for providing a process for aggregating and standardizing healthcare quality ratings comprising:
   a nontransitory computer readable medium;
   and computer program code, encoded on the computer readable medium, comprising computer readable instructions for:
   obtaining healthcare service provider ratings data from two or more different sources of healthcare service provider ratings data, the two or more different sources of healthcare service provider ratings data having different rating systems and being selected from at least one of the group of sources of healthcare service provider ratings data consisting of:
   a healthcare plan provider,
   a healthcare insurance provider,
   a healthcare service provider,
   a third party rating system, and
   a healthcare consumer based healthcare service provider rating system;
   aggregating the healthcare service provider ratings data from the two or more sources of healthcare service provider ratings data;
   standardizing the aggregated healthcare service provider ratings data from the two or more sources of healthcare service provider ratings data by mapping ratings criteria from the two or more ratings systems of the two or more sources of healthcare service provider ratings data to a single ratings system;
   providing healthcare consumers access to the standardized aggregated healthcare service provider ratings data from the two or more sources of healthcare service provider ratings data.

12. The computer program product for providing a process for aggregating and standardizing healthcare quality ratings of claim 11, wherein;
   at least part of the healthcare service provider ratings data obtained from the two or more sources of healthcare service provider ratings data is obtained using screen scraping technology.

13. The computer program product for providing a process for aggregating and standardizing healthcare quality ratings of claim 12, wherein;
   at least part of the healthcare service provider ratings data obtained from the two or more sources of healthcare service provider ratings data is obtained from application output data of at least one application associated with at least one source of healthcare service provider ratings data using screen scraping technology.

14. The computer program product for providing a process for aggregating and standardizing healthcare quality ratings of claim 12, wherein;
   at least part of the healthcare service provider ratings data obtained from the two or more sources of healthcare service provider ratings data is obtained from least one web-site associated with at least one source of healthcare service provider ratings data using screen scraping technology.

15. The computer program product for providing a process for aggregating and standardizing healthcare quality ratings of claim 11, wherein;
   aggregating the healthcare service provider ratings data from the two or more sources of healthcare service provider ratings data comprises aggregating the healthcare service provider ratings data in accordance with one or more aggregation parameters.

16. The computer program product for providing a process for aggregating and standardizing healthcare quality ratings of claim 11, wherein;
   standardizing the aggregated healthcare service provider ratings data from the two or more sources of healthcare service provider ratings data comprises normalizing the aggregated healthcare service provider ratings data from the two or more sources of healthcare service provider ratings data.

17. The computer program product for providing a process for aggregating and standardizing healthcare quality ratings of claim 16, wherein;
   the aggregated healthcare service provider ratings data from the two or more sources of healthcare service provider ratings data is normalized using one or more weighting factors based on one or more weighting parameters.

18. A computing system implemented process for aggregating and standardizing quality ratings comprising:
   Obtaining, by a healthcare quality ratings computing system, healthcare service provider ratings data from two or more different sources of healthcare service provider ratings data, the two or more different sources of healthcare service provider ratings data having different rating systems and being selected from at least one of the group of sources of healthcare service provider ratings data consisting of:
   a healthcare plan provider,
   a healthcare insurance provider,
   a healthcare service provider,
   a third party rating system, and
   a healthcare consumer based healthcare service provider rating system;
   aggregating, by the healthcare quality ratings computing system, the service provider ratings data from the two or more sources of service provider ratings data;
   standardizing, by the healthcare quality ratings computing system, the aggregated service provider ratings data from the two or more sources of service provider ratings data by mapping ratings criteria from the two or more ratings systems of the two or more sources of healthcare service provider ratings data to a single ratings system;
   providing, by the healthcare quality ratings computing system, consumers access to the standardized aggregated service provider ratings data from the two or more sources of service provider ratings data.

19. The computing system implemented process for aggregating and standardizing quality ratings of claim 18, wherein;
   at least part of the service provider ratings data is obtained from at least one of the two or more sources of service provider ratings data by data transfer from the at least one of the two or more sources of service provider ratings data.

20. The computing system implemented process for aggregating and standardizing quality ratings of claim 18, wherein;
   at least part of the service provider ratings data obtained from the two or more sources of service provider ratings data is obtained using screen scraping technology.

21. The computing system implemented process for aggregating and standardizing quality ratings of claim 18, wherein; aggregating the service provider ratings data from the two or more sources of service provider ratings data comprises aggregating the service provider ratings data in accordance with one or more aggregation parameters.

22. The computing system implemented process for aggregating and standardizing quality ratings of claim 18, wherein; standardizing the aggregated service provider ratings data from the two or more sources of service provider ratings data comprises normalizing the aggregated service provider ratings data from the two or more sources of service provider ratings data.

\* \* \* \* \*

UNITED STATES PATENT AND TRADEMARK OFFICE
CERTIFICATE OF CORRECTION

PATENT NO.        : 7,844,472 B1
APPLICATION NO.   : 12/018740
DATED             : November 30, 2010
INVENTOR(S)       : Muhammet Serdar Akin and Michael S. Klieman It is certified that error appears in the above-identified patent and that said Letters Patent is hereby corrected as shown below:

In Column 22, Line 26, Claim 5, replace "from least one" with --from at least one--; and
In Column 23, Line 62, Claim 14, replace "from least one" with --from at least one--.

Signed and Sealed this
Eleventh Day of September, 2012

David J. Kappos
*Director of the United States Patent and Trademark Office*